United States Patent [19]

Koros et al.

[11] Patent Number: 5,688,275
[45] Date of Patent: Nov. 18, 1997

[54] SPINAL COLUMN ROD FIXATION SYSTEM

[76] Inventors: Tibor Koros; Gabriel Koros, both of 610 Flinn Ave., Moorpark, Calif. 93021

[21] Appl. No.: 598,924

[22] Filed: Feb. 9, 1996

[51] Int. Cl.$^6$ ........................................... A61B 17/70
[52] U.S. Cl. ........................................... 606/61; 606/73
[58] Field of Search .................... 606/60, 61, 72, 606/73

[56] References Cited

U.S. PATENT DOCUMENTS

| | | | |
|---|---|---|---|
| 4,743,260 | 5/1988 | Burton | 623/17 |
| 4,854,311 | 8/1989 | Steffe | 128/92 |
| 4,887,595 | 12/1989 | Heinig et al. | 606/61 |
| 5,030,220 | 7/1991 | Howland | 606/61 |
| 5,084,049 | 1/1992 | Asher et al. | 606/61 |
| 5,092,867 | 3/1992 | Harms et al. | 606/61 |
| 5,242,445 | 9/1993 | Ashman | 606/61 |

*Primary Examiner*—Michael Buiz
*Assistant Examiner*—David O. Reip
*Attorney, Agent, or Firm*—Richard D. Slehofer

[57] ABSTRACT

An implantable vertebrae prosthesis for use in aligning and strengthening the adjacent vertebrae in the lumbar region of the spinal column is disclosed. After implantation, the prosthesis maintains a low profile and is usually not felt by the patient after healing. The prosthesis is designed to provide support to the degenerative lumbar region of the spine. The spinal fixation apparatus includes a cortical screw, a connecting rod, a cylindrical plug, an adjustable cap, a block, and a retaining nut which will lock together when the retaining nut is tightened to lock all of the components together as a unit after implantation. The prosthesis is self-locking.

6 Claims, 3 Drawing Sheets

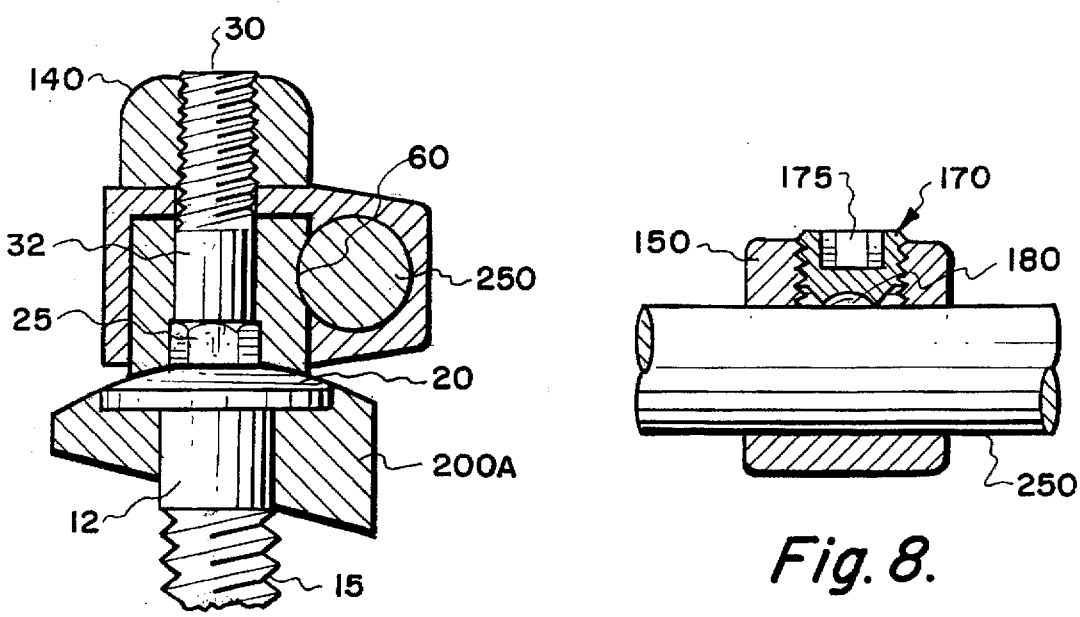
Fig. 5A.
Fig. 8.
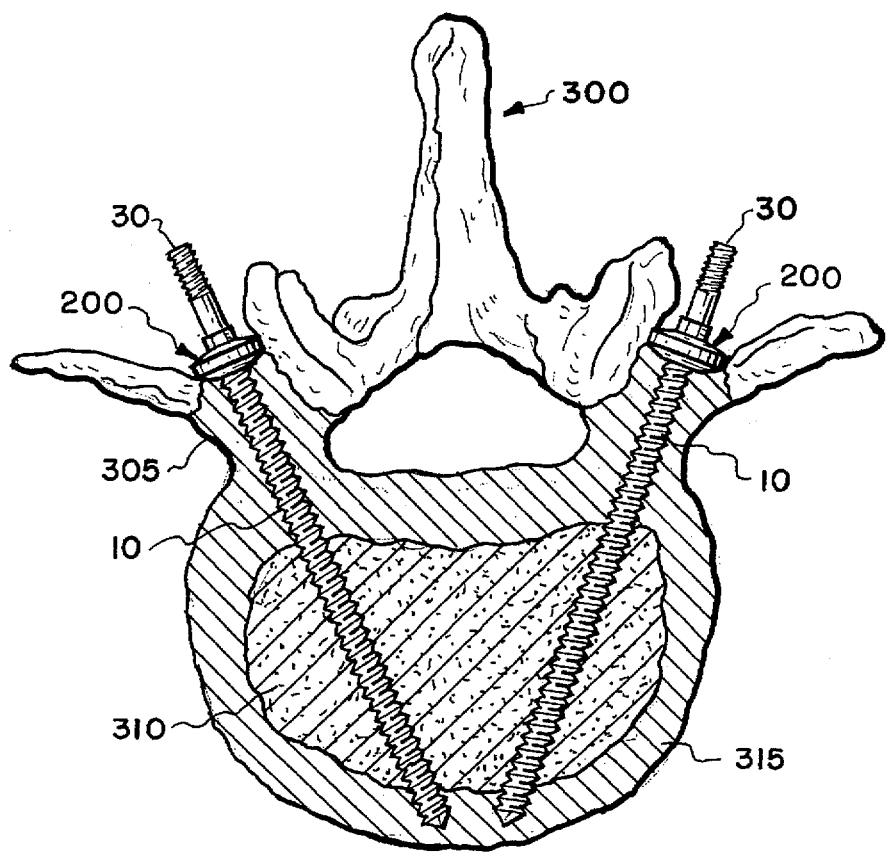
Fig. 9.

SPINAL COLUMN ROD FIXATION SYSTEM

BACKGROUND OF THE INVENTION

1. Field of the Invention

The present invention pertains to the following areas of technology:

SURGERY—Prosthesis (i.e. artificial body member), parts thereof, or aids and accessories therefor. Implantable prosthesis —bone prosthesis; spinal column (e.g. vertebra, spinal disc, etc.,)

2. Description of the Prior Art

U.S. Pat. No. 4,743,260 issued to Burton discloses a method for a flexible stabilization system for a vertebral column.

U.S. Pat. No. 4,854,311 issued to Steffee discloses a bone screw.

The spinal column is commonly referred to as the backbone. The spinal column encloses the spinal cord and consists of 33 vertebrae. The top 7 vertebrae are referred to as the cervical vertebrae. The next lower succeeding 12 vertebrae below the cervical vertebrae are referred to as the thoracic, or dorsal, vertebrae. The next lower succeeding 5 vertebrae below the thoracic vertebrae are referred to as the lumbar vertebrae. The next lower succeeding 5 vertebrae below the lumbar vertebrae are referred to as the sacral vertebrae. In adults, the 5 sacral vertebrae fuse to form a single bone. The next lower succeeding 4 vertebrae below the sacral vertebrae are referred to as the coccygeal vertebrae. Also in adults, the 4 rudimentary coccyx vertebrae fuse to form one bone called the coccyx. The number of vertebrae is sometimes increased by an additional vertebra in one region, and sometimes one may be absent in another.

A typical vertebra consists of a ventral body and a dorsal or neural arch. In the thoracic region the body bears on each side two costal pits for reception of the head of a rib. The arch which encloses the vertebral foramen is formed of two roots or pedicles and two lamina. The arch bears seven processes: a dorsal spinous process, two lateral transverse processes, and four articular processes (two superior and two inferior). A deep concavity, inferior vertebral notch, on the inferior border of the arch provides a passageway for a spinal nerve. The successive vertebral foramina surround the spinal cord.

The bodies of successive vertebrae articulate with one another and are separated by intervertebral disks, disks of fibrous cartilage enclosing a central mass, the nucleus pulposus. The inferior articular processes articulate with the superior articular processes of the next succeeding vertebra in the caudal direction. Several ligaments (supraspinous, interspinous, anterior and posterior longitudinal, and the ligamenta flava) hold the vertebrae in position yet permit a limited degree of movement.

A pedicle is the bony process which projects backward from the body of a vertebra connecting with the lamina on each side. The pedicle forms the root of the vertebral arch.

SUMMARY AND OPERATION OF THE INVENTION

The present invention is an implantable vertebrae prosthesis for use in aligning and strengthening the adjacent vertebrae in the lumbar region of the spinal column. After implantation, the prosthesis maintains a low profile and is usually not felt by the patient after healing. Because of age or injury, the lumbar vertebrae can sometimes lose their ability to remain rigid yet flexible as is the case with a healthy spinal column. Degeneration of the spinal column frequently occurs with age. The vertebrae can slip, degeneration of the individual discs can occur with age, and the individual vertebra may have to be removed partially or completely because of cancer, a tumor, or accident. The present invention is designed to provide support to the degenerative lumbar region of the spine.

FIG. 9 illustrates an elevational view of a lumbar vertebra. A pair of properly implanted cortical screws are also shown in FIG. 9. The hard cortical bony area where the shank of each screw is located is called the pedicle. The center of the vertebra is comprised of soft bone and is referred to as the cortex. The cortex is surrounded by hard bone. The present invention can have a short or a long cortical screw. A short screw is implanted only in the pedicle and is not illustrated. A long screw reaches the base of the cortex as is illustrated in FIG. 9. A short screw can be referred to as a unicortical screw and a long screw can be referred to as a bicortical screw. The surgeon first clears a flat area on the pedicle so that a spacer washer can be seated on the prepared surface. The area is reamed out with a reaming tool. The spacer washer is illustrated in FIG. 3 below the tip of the cortical screw. The spacer washer is important for dispersing the stress placed on the screws after the operation. The spacer washer is preferably 15 millimeters in diameter with a beveled bottom and bore for allowing the cortical screw to pass through. After an area has been cleared by the surgeon by cutting and reaming to seat the spacer washer, the surgeon makes a 5 millimeter diameter hole at the bore of the spacer washer and through the pedicle into the cortex or body of the vertebra so that a cortical screw can be screwed into the pedicle and cortex of the vertebra. After the hole is tapped, a probe is inserted to measure the depth of the hole so that the surgeon will know the correct length of the cortical screw to be used for that hole. The cortical screws can have lengths of 35 to 75 millimeters and can be available in 5 millimeter increments within this range. A cortical screw of 60 to 75 millimeters would be used in the bicortical implantation as illustrated in FIG. 9. Furthermore, the surgeon has to deal with vertebrae that are not in alignment because of the condition and relative location of the vertebrae. The surgeon wants the top of the projecting stems of the cortical screws to be aligned as much as possible. In order to accomplish this, the spacer washer is used and which slips onto the shank portion of the cortical screw. The spacer washer can have 3 to 5 millimeter thickness. Various thicknesses of spacer washers will be available for the surgeon. By determining the depth of the tapped hole, the surgeon can choose the appropriate length of the cortical screw and a correct size spacer washer so that the top stem of the cortical screw will be the same height as the other cortical screw stems that are to be inserted on the adjacent pedicles on the same side of the spinal column. Additionally, the bottom tip of the cortical screw cannot penetrate beyond the anterior circumference of the cortex of the vertebra. The aorta lies adjacent to the anterior circumference of the vertebral column. A cortical screw which extends beyond the vertebra could puncture the aorta. The stem portion above the cortical screw has a hex-shaped base to receive a socket tool so that the cortical screw can be threaded into the vertebra. The cortical screw will be tightened until the screw head mates with the top of the spacer washer, and then will be sufficiently tightened according to the judgment of the surgeon. The spacer washer and the cortical screw are then considered to be one integral piece. After the operation, all stress placed on the screw will be transferred to and dispersed by the spacer washer. The illustration in FIG. 1 shows 3 adjacent cortical screws on one side of the spinal column, and 3 adjacent cortical screws on the other side of the spinal column. Each cortical screw has a projecting stem and a hex nut projection at its base so that a small socket can be slipped over the top of the screw to allow an instrument to rotate the screw to screw it into place. After the three or more cortical screws have been screwed into place, the next step is to insert a rod between the three screws. The rod provides the rigidity for the spinal column. A cylindrical plug having a bore is first placed over each stem on each screw. Then a hollow cap is placed over the plug and the stem. The cap has a transverse bore so that a block with a transverse arm can be passed through the bore in the cap. A retaining nut is then loosely threaded on the end of the projecting stem of the screw. The block has a bore for allowing the rod to pass through. The rod is inserted into all three bore holes in the adjacent blocks. The combination of the block, the cap, and the plug allows for an adjustable articulated linkage and clamp between the rod and the cortical screws. The rod and clamps are adjusted to the desired low profile position. The retaining nut is then tightened to clamp the cap and plug in place on the screw. The final step is to tighten the setscrew in each of the blocks to clamp the rod in the three blocks. The bottom of the setscrew is concave to allow its circumference to clamp at two pressure points to retain the rod in place. The setscrew prevents axial or rotational movement of the interconnecting rod. The system is completely self-locking. The pair of interconnecting rods on both sides of the vertebrae form a bridge between the adjacent vertebrae. Retracted muscles and soft tissue are then released to allow them to cover the rod system. After suturing, the operation is complete. The self-locking clamps, rod and cortical screws will remain securely in place long after the operation. The three vertebrae will remain rigid as a unit.

BRIEF DESCRIPTION OF THE DRAWINGS

FIG. 5A is a cross-sectional view similar to FIG. 5 illustrating the wedge-shaped washer in place of the bevel-shaped washer.

FIG. 8 is an enlarged longitudinal sectional view as circled in FIG. 6 of the setscrew bearing against the rod.

FIG. 9 is an elevational view of a partial sectional view of a lumbar vertebra illustrating a pair of cortical screws with their respective spacer washers properly positioned in a bicortical implantation. The pair of screws form a 30 to 40 degree arc.

DETAILED DESCRIPTION OF THE INVENTION

Figure 1:
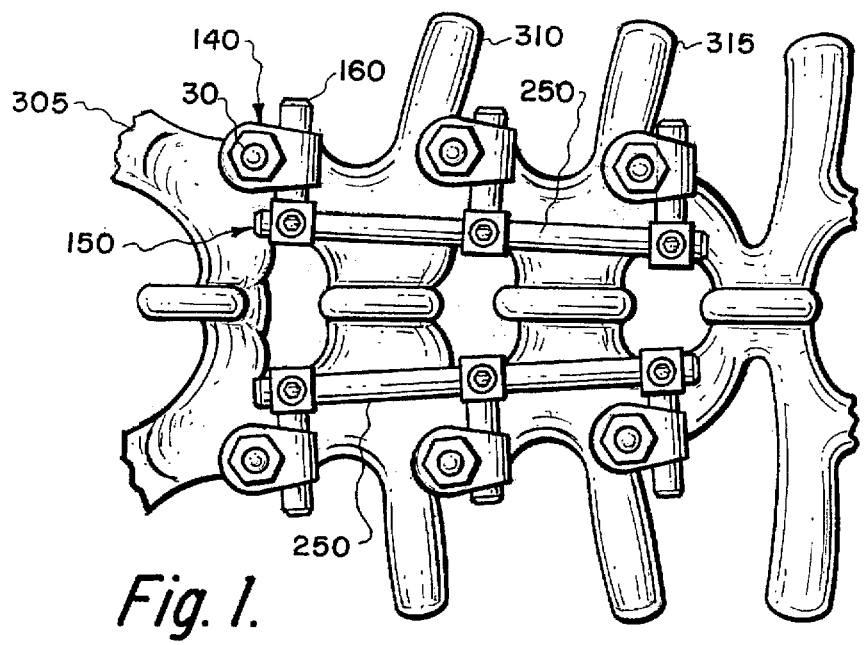
FIG. 1 is a top plan view of the left and right spinal rod system correctly positioned on the lower spine of a hypothetical patient.
Figure 2:
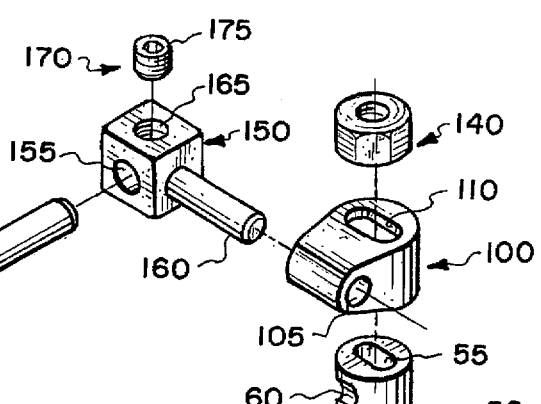
FIG. 2 is a perspective view of the rod, clamp, and the cortical screw.

The present invention will now be discussed in detail. The present invention consists of a combination cortical screw 10, an adjustment plug 50, an adjustable cap 100, a retaining nut 140, a block 150, a spacer washer 200, and an interconnecting rod 250.

The combination cortical screw 10 includes four portions or components. They are the lower screw portion 15, the rounded head 20, the hex base 25 located immediately above the head 20, and the stem 30 extending axially from and above the head 20. All of the screw components, which comprise the cortical screw, are in axial alignment. The lower screw portion 15 can range from 30 to 75 millimeters in length and available in 5 millimeter increments. The diameter of the screw 15 can be from 4 to 8.5 millimeters. The threads are similar to a wood screw in that the root is wide and the thread crest is sharp. The threads are ASTM standard threads. The head portion 20 is similar to a round head on a screw. A small shank 12 is provided between the bottom of the head 20 and the termination of the threads 15. The shank portion 12 is smooth and can receive a spacer washer 200. The head 20 should be at least 5 millimeters in diameter. The top of the head has the stem 30 extending upwardly and axially. The diameter of the stem 30 can be less than the diameter of the lower screw 15. The stem can be about 15 millimeters in length and about 3 to 5 millimeters in diameter. The base 25 of the stem is shaped like a small hex nut. Above the hex base 25 is the shank portion 32 which is followed by a threaded portion 34. The upper portions of the clamp are clearly illustrated in FIG. 5.

The hex base 25 is used for receiving a small socket so that the combination screw 10 can be screwed into the pedicle 305, cortex 310 and into the anterior bony cortex 315 of the vertebra 300. The properly positioned screw 10 in the lumbar vertebra is clearly illustrated in FIG. 9. An appropriate tool can be attached to the small socket so that the cortical screw 10 can be easily turned by the surgeon.

A cylinder-shaped adjustment plug 50 is designed to fit over the screw stem 30. The plug 50 has a smaller diameter than the diameter of the screw head 20. The plug 50 has an axial stepped bore 55. The bottom of the bore is of sufficient diameter to fit over the hex base 25 of the stem 30. The top of the bore 55 is oval-shaped. The bore then tapers downwardly to a circular shape. The outside cylinder wall of the plug 50 has a transverse indentation 60, which use will be described later. The indentation 60 can be described as resembling part of the wall of a cylinder. The axis of the indentation is parallel with the longitudinal axis of the oval opening of the bore 55.

The cap 100 is shaped like a cam. A cylindrical cavity is formed at the bottom of the cap and extends vertically to just below the top of the cap. An oval slot 110 is cut into the top of the cap. The center of the oval slot is aligned with the axis of the cylindrical cavity. The eccentric cam area has a transverse smooth bore 105 drilled therethrough. The axis of the cylindrical cavity and the axis of the smooth bore 105 are perpendicular to each other. The smooth bore 105 cuts an opening into the cylindrical cavity midway between the ends of the smooth bore 105. The opening corresponds with the indentation 60 on the adjustment plug 50 so that when the indentation 60 is properly aligned with the smooth bore 105 on the cap 100, a smooth unbroken cylindrical bore results.

Figure 3:
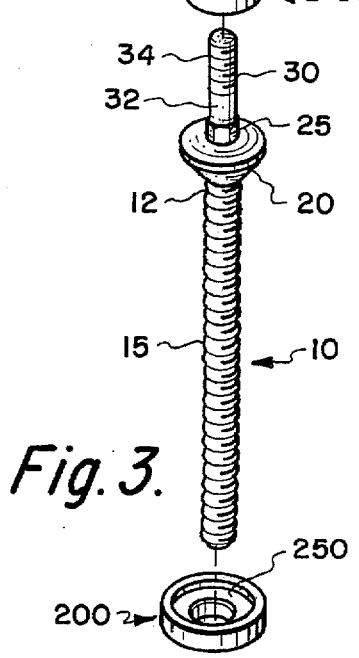
FIG. 3 is an exploded perspective view of the rod, clamp and the cortical screw as shown in FIG. 2.
Figure 4:
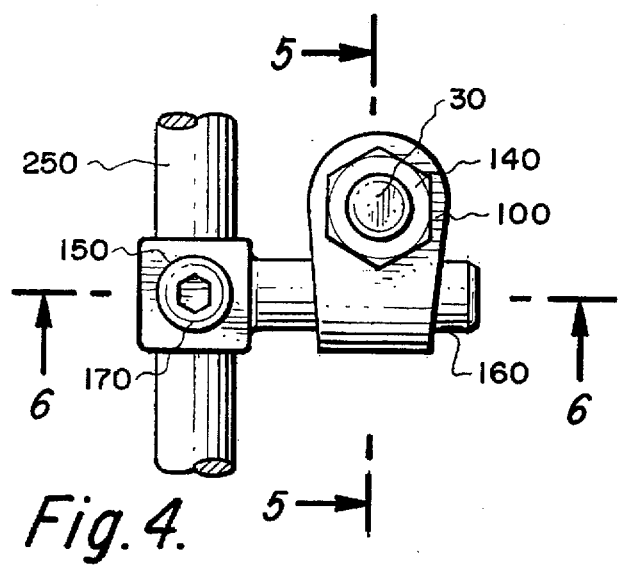
FIG. 4 is a top plan view of the rod, clamp, and cortical screw as shown in FIG. 2.

The block 150, which is clearly illustrated in FIG. 3, has six faces and has a smooth cylindrical bore 155 drilled therethrough between two opposed faces. The bore 155 is positioned in the center area of the opposed pair of faces on the block 150. An integral transverse arm 160 extends from a face opposite either bore face. The arm 160 is similar to a rod and extends perpendicular to the axis of the bore 155. An internal threaded hole 165 for receiving a setscrew 170 is tapped into the top face of the block 150. The internal screw 165 is perpendicular to the bore 155 and terminates in the bore 155. The internal screw 165 is used to receive an external threaded setscrew 170.

After the surgeon has implanted the necessary plurality of combination cortical screws 10 in the vertebrae of the patient being operated on, the next step is to secure the clamps and interconnecting rod 250, and then to tighten everything.

The clamp comprising the adjustment plug 50, the cap 100, the retaining nut 140, and the block 150 with the transverse arm 160 would be preassembled before the operation in order to save time. A sterile material can be placed on the tip of the transverse arm 160 to prevent it from dislodging from the cap 100. The material is removed later.

Figure 5:
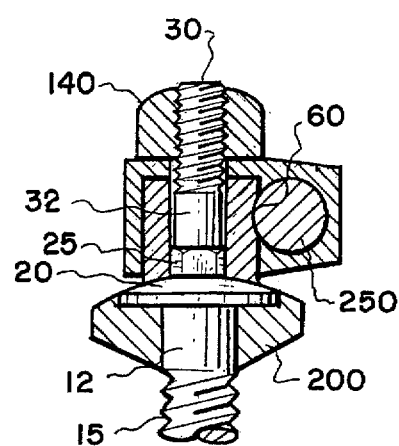
FIG. 5 is a cross-sectional view taken along the line 5—5 in FIG. 4.
Figure 6:
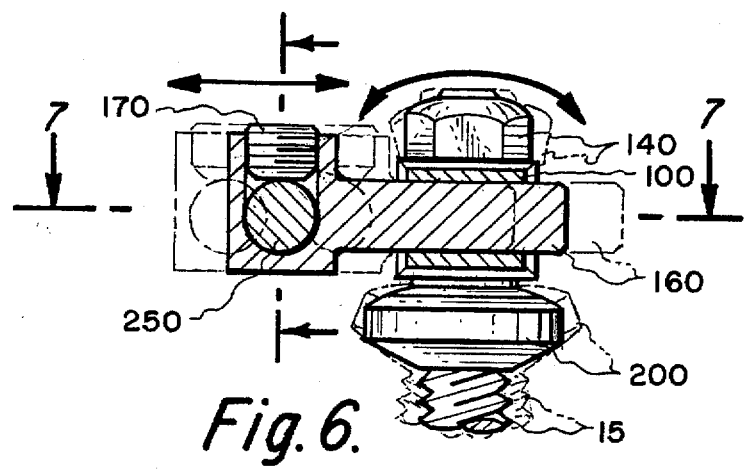
FIG. 6 is a cross-sectional view taken along the line 6—6 in FIG. 4.
Figure 7:
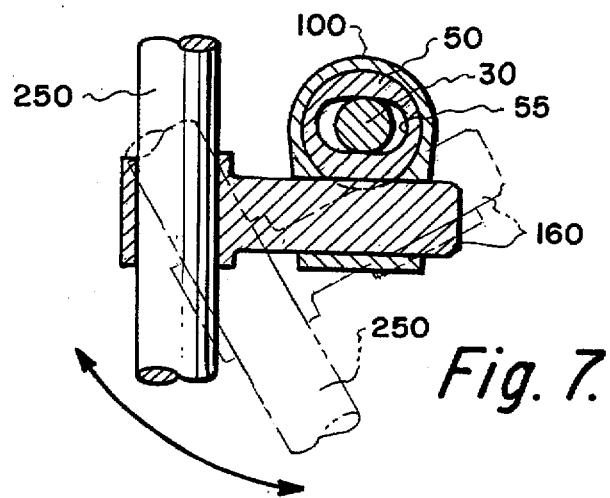
FIG. 7 is a cross-sectional view taken along the line 7—7 in FIG. 6.

The head 20 on the cortical screw 10 is slightly dome-shaped, which is clearly illustrated in cross section in FIG. 5. The base of the plug 50 is ring-shaped as a result of a disc-shaped depression cut into the base of the plug. This ringed base allows the plug 50 to pivot on the head 20 and also swivel on the stem 30 on the screw. The circular-to-oval-shaped bore 55 on the plug 50 allows the plug 50 to pivot or rock back and forth about the head portion 20 of the cortical screw 10 in one plane. The curved double arrow in FIG. 6 illustrates the pivotal capability of the clamp relative to the cortical screw 10. The straight double arrow illustrates the extension and retraction capability of the transverse block arm 160 relative to the clamp to adjust the distance of the interconnecting rod 250 relative to the implanted cortical screw 10. FIG. 7 illustrates the swivel capability of the clamp relative to the interconnecting rod 250 to adjust the axis of the rod 250 relative to the implanted cortical screw 10. The transverse arm 160 extending from the block 150, which is inserted in the bore 105 of the cap 100, keeps the oval opening in the top of the bore 55 and the oval slot 110 in the top of the cap 100 superimposed relative to each other. The arm 160 prevents the plug 50 from dislodging from the cap 100 and also keeps the plug 50 in proper alignment relative to the cap 100. The top of the cap 100 surrounding the oval slot 110 is slightly dome-shaped. This allows the retaining nut 140 to make good contact with the top of the cap 100, and the dome-shaped surface acts as a spring to press against the tightened nut 140 to prevent it from loosening.

The retaining nut 140 is smooth and rounded on the top and has a threaded bore so that it can be threaded onto the threaded portion 34 of the stem 30 of the combination cortical screw 10. The height or length of the stem 30 is more than the height or thickness of the cap 100 so that the threaded end 34 portion of the stem 30 is exposed to receive the retaining nut 140. As the retaining nut 140 is tightened, the self-locking features of the present invention become readily apparent. The transverse arm 160 on the block 150, which has been previously inserted in the side bore 105 in the cap 100, is pressed down by the cap 100 and the plug 50. This locks the transverse arm 160 and prevents longitudinal or rotational movement of the transverse arm 160. The tightened retaining nut 140 also locks the pivoted and swivel position of the cap 100 and plug 50. Of course, prior to tightening the retaining nut 140, the interconnecting rod 250 has already been inserted in the plurality of aligned clamps. After the retaining nut 140 has been tightened to a recommended torque setting, the setscrew 170 in each block 150 is tightened. The top of the setscrew has an allen head recess 175 for receiving an allen head wrench. The tip of the setscrew is flat with a disc-shaped depression or a concave surface so that the rim 180 formed presses against the interconnecting rod 250 in two places to prevent any movement of the rod in the block after the surgery. The setscrew 170 pressing against the rod 250 is illustrated in an enlarged fragment sectional view in FIG. 8. The tightened setscrew prevents longitudinal or rotational movement of the interconnecting rod 250.

The spacer washer 200 has a disc-shaped recess 205 of the same diameter as the round head 20 on the cortical screw 10 so that the top of the spacer washer 200 seats around the circumference of the head 20 on the screw 10. This is clearly illustrated in FIG. 5. The bottom of the spacer washer is beveled. This beveled feature allows the bottom to seat itself on the pedicle after the surgeon has prepared the surface by reaming and snipping. When the cortical screw is inserted in the sacrum, the spacer washer 200a should be wedge-shaped. The wedge shape will compensate for the slope of the sacrum relative to the L5 lumbar vertebra. The wedge shaped washer causes the cortical screw to be more in a vertical alignment.

FIG. 1 illustrates the present invention properly positioned on the sacrum 320, the fifth lumbar vertebra 325 and the fourth lumbar vertebra 330. Three clamps and a rod are positioned on the left side of the spine, and three clamps and a rod are positioned parallel on the right side of the spine. The interconnecting rod is rigid and straight. The surgeon can bend the rod prior to placing it in the three adjacent clamps, if the alignment of the clamps and the vertebrae require a bent rod. Cross-clamps or braces can be provided to strengthen the pair of rod systems, if necessary.

While the present invention has been shown and described herein in what is conceived to be the best mode contemplated, it is recognized that departures may be made therefrom within the scope of the invention which is therefore not to be limited to the details disclosed herein, but is to be afforded the full scope of the invention.

What is claimed is:

1. A spinal fixation apparatus for permanently holding a spinal rod in place, comprising:

a cortical screw having a lower screw portion, a medial head, and a threaded upper stem, said medial head having a top surface and a bottom surface:

a cylindrical plug having a circular-to-oval-shaped axial bore cooperating with said upper stem and resting on said medial head of said cortical screw, said plug having an indentation in an outer wall;

an adjustable cap having a vertical cylindrical chamber open at the bottom for holding said cylindrical plug and an oval slot at the top for allowing said upper stem of said cortical screw to extend upwardly through said oval slot, said cap having a bore perpendicular to said cylindrical chamber;

a block having a transverse arm, a bore, and an internally threaded hole perpendicular to and cooperating with said bore in said block; and a retaining nut for cooperating with the threaded upper stem so that said retaining nut, said cap, said plug, and said cortical screw form a clamping assembly for said transverse arm;

wherein said bore in said cad and said indentation in said plug are alignable so that said transverse arm can slide into and through said bore in said cap and fix said plug in a position to superimpose said circular-to-oval-shaped axial bore in said plug with said oval slot in said cap, and wherein tightening of said retaining nut against said cap clamps said transverse arm and prevents rotational and longitudinal movement of said transverse arm relative to said clamping assembly.

2. The spinal fixation apparatus as recited in claim 1 further comprising:

an interconnected rod inserted in said bore in said block; and a setscrew having a top portion and a lower tip portion and sized for cooperating with said internally threaded hole in said block;

wherein said setscrew can be turned to lock said interconnecting rod in place to prevent rotational and longitudinal movement of said rod in said bore in said block.

3. The setscrew as recited in claim 2 wherein the lower tip portion of said setscrew has a disc-shaped depression and a rim for creating two pressure points against said rod.

4. The spinal fixation apparatus as recited in claim 1 further comprising:

a spacer washer having a top surface, a bottom surface and a center bore, said center bore sized for sliding engagement with said cortical screw and said top surface of said spacer washer configured for cooperating with said bottom surface of said medial head on said cortical screw.

5. The spacer washer as recited in claim 4 wherein:

said top surface of said spacer washer has a disk-shaped depression for receiving and mating with said bottom surface of said medial head to form an integral connection; and said bottom surface of said washer has a beveled shape for cooperating with a prepared surface of a pedicle area on a vertebra;

said washer dispersing any forces applied to said cortical screw after said cortical screw is implanted in the vertebra.

6. The spacer washer as recited in claim 4 wherein:

said top surface of said spacer washer has a disc-shaped depression for receiving and mating with said bottom surface of said me dial head to form an integral connection; and said bottom surface of said washer has a slanted shape forming a wedge-shaped washer for cooperating with a surface of a sacrum;

said washer dispersing any forces applied to said cortical screw after said cortical screw is implanted in the sacrum.

* * * * *